(12) United States Patent
Cockerill et al.

(10) Patent No.: US 9,809,575 B2
(45) Date of Patent: Nov. 7, 2017

(54) PHARMACEUTICAL COMPOUNDS

(71) Applicant: re:Viral Ltd, London (GB)

(72) Inventors: Stuart Cockerill, London (GB); Christopher Pilkington, London (GB); James Lumley, London (GB); Richard Angell, London (GB); Neil Mathews, London (GB)

(73) Assignee: ReViral Limited, Stevenage (GB)

( * ) Notice: Subject to any disclaimer, the term of this patent is extended or adjusted under 35 U.S.C. 154(b) by 624 days.

(21) Appl. No.: 14/357,293

(22) PCT Filed: Nov. 12, 2012

(86) PCT No.: PCT/GB2012/052806
§ 371 (c)(1),
(2) Date: May 9, 2014

(87) PCT Pub. No.: WO2013/068769
PCT Pub. Date: May 16, 2013

(65) Prior Publication Data
US 2014/0308282 A1    Oct. 16, 2014

(30) Foreign Application Priority Data
Nov. 10, 2011   (GB) .................................. 1119538.5

(51) Int. Cl.
| | |
|---|---|
| *C07D 403/06* | (2006.01) |
| *A61K 31/4184* | (2006.01) |
| *A61K 31/437* | (2006.01) |
| *A61K 31/4747* | (2006.01) |
| *A61K 31/5386* | (2006.01) |
| *C07D 401/06* | (2006.01) |

(Continued)

(52) U.S. Cl.
CPC ........ *C07D 403/06* (2013.01); *A61K 31/4184* (2013.01); *A61K 31/437* (2013.01); *A61K 31/4747* (2013.01); *A61K 31/5386* (2013.01); *A61K 31/5513* (2013.01); *A61K 45/06* (2013.01); *C07D 401/06* (2013.01); *C07D 413/06* (2013.01); *C07D 471/10* (2013.01); *C07D 498/10* (2013.01)

(58) Field of Classification Search
None
See application file for complete search history.

(56) References Cited

U.S. PATENT DOCUMENTS

| | | |
|---|---|---|
| 4,044,136 A | 8/1977 | Danilewicz et al. |
| 2002/0099208 A1 | 7/2002 | Yu et al. |

(Continued)

FOREIGN PATENT DOCUMENTS

| | | |
|---|---|---|
| CN | 1898247 A | 1/2007 |
| JP | 2003-503401 A | 1/2003 |

(Continued)

OTHER PUBLICATIONS

Andrews et al., "Pyrrolidine-5,5-trans-lactams. 1. Synthesis and Incorporation into Inhibitors of Hepatitis C Virus NS3/4A Protease", *Organic Letters*, vol. 4, No. 25, pp. 4475-4478 (2002).

(Continued)

*Primary Examiner* — Jeffrey S Lundgren
*Assistant Examiner* — Tori M Strong
(74) *Attorney, Agent, or Firm* — Leydig, Voit & Mayer, Ltd.

(57) ABSTRACT

Benzimidazoles of formula (I): wherein: A is 5- to 12-membered aryl or 5- to 12-membered heteroaryl, each of which is unsubstituted or substituted; Y is a single bond, —$(CH_2)_p$—, —X—, —$CH_2$—X—, or —X—$CH_2$—; X is —O—, —S—, —N($R^2$)—, >C=O, >S(=O), >S(=O)$_2$, —O—C(=O)—, —C(=O)—O—, N($R^2$)—C(=O)—, or —C(=O)—N($R^2$)—; each L is independently a single bond, $C_{1-3}$alkylene, $C_{2-3}$alkenylene or $C_{2-3}$alkynylene; $R^1$ is $C_{1-6}$alkyl, $C_{2-6}$alkenyl or $C_{2-6}$alkynyl, each of which is unsubstituted or substituted; each Z is independently —N($R^2$)$_2$, —O$R^2$, —S$R^2$, —S(=O)$R^2$, —S(=O)$_2R^2$; each $R^2$ is independently hydrogen, $C_{1-6}$alkyl, $C_{2-6}$alkenyl or $C_{2-6}$alkynyl, wherein said alkyl, alkenyl and alkynyl groups are unsubstituted or substituted; m is 0, 1, 2, or 3; n is 1, 2, or 3; and p is 1, 2, or 3; and the pharmaceutically acceptable salt thereof are inhibitors of RSV and can therefore be used to treat or prevent an RSV infection.

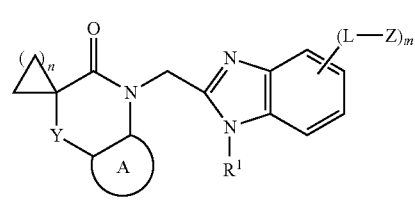

Formula (I)

10 Claims, No Drawings

(51) Int. Cl.
    *C07D 413/06*     (2006.01)
    *C07D 471/10*     (2006.01)
    *A61K 31/5513*     (2006.01)
    *A61K 45/06*     (2006.01)
    *C07D 498/10*     (2006.01)

(56) References Cited

U.S. PATENT DOCUMENTS

| | | |
|---|---|---|
| 2010/0278835 A1 | 11/2010 | Blade et al. |
| 2011/0144106 A1 | 6/2011 | Chen et al. |

FOREIGN PATENT DOCUMENTS

| | | | | |
|---|---|---|---|---|
| WO | WO 0132171 A1 * | 5/2001 | ........... | C07D 209/10 |
| WO | WO 02/062290 A2 | 8/2002 | | |
| WO | WO 03/053344 A2 | 7/2003 | | |
| WO | WO 2005/061513 A1 | 7/2005 | | |
| WO | WO 2010/103306 A1 | 9/2010 | | |

OTHER PUBLICATIONS

Meanwell et al., "Respiratory syncytial virus—the discovery and optimization of orally bioavailable fusion inhibitors", *Drugs of the Future*, vol. 32, No. 5, pp. 441-455 (2007).
Search Report in corresponding Chinese Patent Application No. 201280066542.8, dated Feb. 26, 2015.
International Preliminary Report on Patentability in corresponding International Patent Application No. PCT/GB2012/052806, dated May 13, 2014.
International Search Report in corresponding International Patent Application No. PCT/GB2012/052806, dated Nov. 12, 2012.
Combrink, Keith D., et al., "Respiratory syncytial virus fusion inhibitors. Part 6: An examination of the effect of structural variation of the benzimidazol-2-one heterocycle moiety," *Bioorganic & Medicinal Chemistry Letters*, vol. 17, No. 17, pp. 4784-4790 (2007).
Meanwell, Nicholas A. et al., "Respiratory syncytial virus—the discovery and optimization of orally bioavailable fusion inhibitors," *Drugs of the Future*, vol. 32, No. 5, pp. 441-455 (2007).

* cited by examiner

PHARMACEUTICAL COMPOUNDS

CROSS-REFERENCE TO RELATED APPLICATIONS

This patent application is a U.S. National Phase Application of International Patent Application No. PCT/GB2012/052806, filed Nov. 12, 2012, which claims the benefit of UK Patent Application No. 1119538.5, filed Nov. 10, 2011, both of which are hereby incorporated by reference in their entireties.

FIELD OF THE INVENTION

The present invention relates to benzimidazole compounds and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occurs in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Additionally, several compounds have been proposed as inhibitors of RSV, including benzimidazole-based compounds. For example, K D Combrink et al., Bioorganic & Medicinal Chemistry Letters, 17 (2007), 4784-4790 discloses the compound BMS-433771 and variants thereof. Further benzimidazole-based compounds are disclosed in WO-02/062290, WO-03/053344 and WO-10/103306.

SUMMARY OF THE INVENTION

It has now been found that a novel series of benzimidazoles are active as RSV inhibitors. The compounds possess reduced lipophilic properties, advantageous pharmacokinetic and toxicological properties and can be readily formulated for pharmaceutical use.

Accordingly, the present invention provides a compound which is a benzimidazole of formula (I):

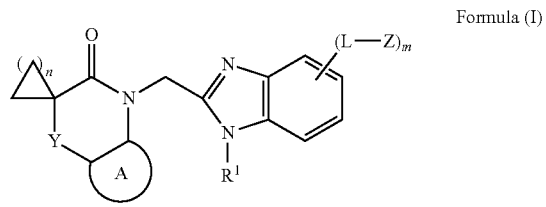

Formula (I)

wherein:
A is 5- to 12-membered aryl or 5- to 12-membered heteroaryl, each of which is unsubstituted or substituted;
Y is a single bond, $-(CH_2)_p-$, $-X-$, $-CH_2-X-$, or $-X-CH_2-$;
X is $-O-$, $-S-$, $-N(R^2)-$, $>C=O$, $>S(=O)$, $>S(=O)_2$, $-O-C(=O)-$, $-C(=O)-O-$, $-N(R^2)-C(=O)-$, or $-C(=O)-N(R^2)-$;
each L is independently a single bond, $C_{1-3}$ alkylene, $C_{2-3}$ alkenylene or $C_{2-3}$ alkynylene;
$R^1$ is $C_{1-6}$ alkyl, $C_{2-6}$ alkenyl or $C_{2-6}$ alkynyl, each of which is unsubstituted or substituted;
each Z is independently $-N(R^2)_2$, $-OR^2$, $-SR^2$, $-S(=O)R^2$, $-S(=O)_2R^2$;
each $R^2$ is independently hydrogen, $C_{1-6}$ alkyl, $C_{2-6}$ alkenyl or $C_{2-6}$ alkynyl, wherein said alkyl, alkenyl and alkynyl groups are unsubstituted or substituted;
m is 0, 1, 2, or 3;
n is 1, 2, or 3; and
p is 1, 2, or 3;
or a pharmaceutically acceptable salt thereof.

DETAILED DESCRIPTION OF THE INVENTION

When any group, ring, substituent or moiety defined herein is substituted, it is typically substituted by Q as defined below.

A $C_{1-6}$ alkyl group or moiety is linear or branched. A $C_{1-6}$ alkyl group is typically a $C_{1-4}$ alkyl group, or a $C_{4-6}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e.

3-methylpentan-3-yl) and neopentyl (i.e. 3,3-dimethylbutan-1-yl). For the avoidance of doubt, where two alkyl moieties are present in a group, the alkyl moieties may be the same or different. A $C_{1-6}$ alkyl group is unsubstituted or substituted, typically by one or more groups Q as defined below. For example, a $C_{1-6}$ alkyl group is unsubstituted or substituted by 1, 2 or 3 groups Q as defined below.

Q is halo, nitro, —CN, OH, $C_{1-6}$ alkoxy, $C_1$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, —$S(=O)_2R'''$, $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

A $C_{1-3}$ alkylene group or moiety is an unsubstituted or substituted, linear or branched, saturated divalent aliphatic hydrocarbon group or moiety containing 1 to 3 carbon atoms. Examples include methylene, ethylene, n-propylene and i-propylene groups and moieties. When the alkylene group is substituted it is typically substituted by a group Q as defined above.

A $C_{2-6}$ alkenyl group is an unsubstituted or substituted, linear or branched hydrocarbon radical of two to six carbon atoms with at least one site of unsaturation, i.e., a carbon-carbon $sp^2$ double bond. An alkenyl group may have "cis" or "trans" orientation, or alternatively "E" or "Z" orientation. Typically it is a $C_{2-4}$ alkenyl group or a $C_{4-6}$ alkenyl group. Examples include ethylenyl or vinyl (—CH=$CH_2$), and allyl (—$CH_2$CH=$CH_2$). When the alkenyl group is substituted it is typically substituted by a group Q as defined above.

A $C_{2-3}$ alkenylene group or moiety is linear or branched, unsaturated divalent aliphatic hydrocarbon group or moiety containing two or three carbon atoms with at least one carbon-carbon $sp^2$ double bond. An alkenylene group may have "cis" or "trans" orientation, or alternatively "E" or "Z" orientation. Examples include —CH=CH—, —CH=$CHCH_2$— and —$CH_2$CH=CH— groups and moieties.

A $C_{2-6}$ alkynyl group is an unsubstituted or substituted, linear or branched hydrocarbon radical of two to six carbon atoms with at least one site of unsaturation, i.e., a carbon-carbon sp triple bond. Typically it is a $C_{2-4}$ alkynyl group or a $C_{4-6}$ alkynyl group. An alkynyl group may have "cis" or "trans" orientation, or alternatively "E" or "Z" orientation. Examples include ethynyl (—C≡CH) or propynyl (propargyl, —$CH_2$C≡CH). When an alkynyl group is substituted it is typically substituted by one or more groups Q as defined above A $C_{2-3}$ alkynylene group is a linear, unsaturated divalent aliphatic hydrocarbon group or moiety containing two or three carbon atoms with one carbon-carbon sp triple bond. An alkynylene group may have "cis" or "trans" orientation, or alternatively "E" or "Z" orientation. Examples include —C≡C—, —C≡$CCH_2$— and —$CH_2$C≡C— groups and moieties.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups Q as defined.

A $C_{1-6}$ alkylthio group is linear or branched. It is typically a $C_{1-4}$ alkylthio group, for example a methylthio, ethylthio, propylthio, i-propylthio, n-propylthio, n-butylthio, sec-butylthio or tert-butylthio group. A $C_{1-6}$ alkylthio group is unsubstituted or substituted, typically by one or more groups Q as defined.

A halogen or halo group is F, Cl, Br or I. Preferably it is F, Cl or Br. A $C_{1-6}$ alkyl group substituted by halogen may be denoted "$C_{1-6}$ haloalkyl", which means a $C_{1-6}$ alkyl group as defined above in which one or more hydrogens is replaced by halo. Likewise a $C_{1-6}$ alkoxy group substituted by halogen may be denoted "$C_{1-6}$ haloalkoxy", which means a $C_{1-6}$ alkoxy group as defined above in which one or more hydrogens is replaced by halo. Typically, $C_{1-6}$ haloalkyl or $C_{1-6}$ haloalkoxy is substituted by 1, 2 or 3 said halogen atoms. Haloalkyl and haloalkoxy groups include perhaloalkyl and perhaloalkoxy groups such as —$CX_3$ and —$OCX_3$ wherein X is a halogen, for example —$CF_3$— $CCl_3$—$OCF_3$ and —$OCCl_3$.

A $C_{1-6}$ hydroxyalkyl group is a $C_{1-6}$ alkyl group as defined above, substituted by one or more OH groups. Typically, it is substituted by one, two or three OH groups. Preferably, it is substituted by a single OH group.

A 5- to 12-membered aryl group is an aromatic carbocyclic group containing from 5 to 12 carbon atoms, for instance from 6 to 10 carbon atoms, such as 6 or 10 carbon atoms. It is monocyclic or a fused bicyclic ring system in which an aromatic ring is fused to another aromatic carbocyclic ring. Examples of a 5- to 12-membered aryl group include phenyl and naphthalenyl. When substituted, an aryl group is typically substituted by $C_{1-4}$ alkyl or a group Q as defined above, for instance by 1, 2 or 3, groups selected from a $C_{1-4}$ alkyl group and a group Q as defined above.

An aralkyl group is an aryl group, as defined above, attached to an alkyl group, as defined above. Examples include benzyl.

A $C_{3-10}$ cycloalkyl group is a saturated hydrocarbon ring having from 3 to 10 carbon atoms. A $C_{3-10}$ cycloalkyl group may be, for instance, $C_3$-$C_7$ cycloalkyl such as cyclopropyl, cyclobutyl, cyclopentyl, cyclohexyl, or cycloheptyl. Typically it is $C_3$-$C_6$ cycloalkyl, for example cyclopropyl, cyclobutyl or cyclopentyl. In one embodiment it is cyclopropyl. A $C_{3-10}$ cycloalkyl group is unsubstituted or substituted, typically by one or more groups Q as defined above.

A 5- to 12-membered heteroaryl group or moiety is a 5- to 12-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, pyridyl and pyrimidyl groups are preferred. When substituted, a heteroaryl group is typically substituted by one or more, e.g. 1, 2 or 3, groups selected from $C_{1-4}$ alkyl and a group Q as defined above. A 5- to 10-membered heterocyclyl moiety is a monocyclic or bicyclic non-aromatic, saturated or unsaturated $C_{5-10}$ carbocyclic ring, in which at least one, for example 1, 2 or 3, carbon atoms in the ring are replaced with an atom or group selected from O, S, SO, $SO_2$, CO and N. Typically, it is a saturated $C_{5-10}$ ring in which 1, 2 or 3 of the carbon atoms in the ring are replaced with an atom or group selected from O, S, $SO_2$, CO and NH. More typically it is a monocyclic ring, preferably a monocyclic $C_5$-$C_6$ ring. Examples include piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl moieties.

For the avoidance of doubt, although the above definitions of heteroaryl and heterocyclyl groups refer to an "N" atom which can be present in the ring, as will be evident to a skilled chemist the N atom will be protonated (or will carry a substituent as defined above) if it is attached to each of the adjacent ring atoms via a single bond. Such protonated forms are embraced within the present definitions of heteroaryl and heterocyclcyl groups.

In formula (I) as defined above, A is typically unsubstituted. In one embodiment A is phenyl or a 5- or 6-membered N-containing heteroaryl group. For instance, A is phenyl or pyridyl.

In formula (I) as defined above Y is typically a single bond, —O—, —C(=O)—N($R^2$)—, or —($CH_2$)$_p$—. Preferably, Y is a single bond, —O—, —C(=O)—NH, or —$CH_2$—. For the avoidance of doubt, the left hand side of the divalent Y moieties as depicted herein is attached to the ring A, and the right hand side is attached to the bridgehead carbon atom of the spiro moiety.

In formula (I) each L is typically $C_{1-3}$ alkylene. In one embodiment each L is —$CH_2$—.

$R^1$ is typically unsubstituted. In one embodiment, $R^1$ is $C_{1-6}$ alkyl. In another embodiment $R^1$ is branched $C_{3-6}$ alkyl, branched $C_{3-6}$ alkenyl or branched $C_{4-6}$ alkynyl. Typically, $R^1$ is branched $C_{4-6}$ alkyl. Preferably $R^1$ is isopentyl.

Each $R^2$ is typically H or $C_{1-4}$ alkyl. More typically, each $R^2$ is H or methyl. Preferably each $R^2$ is H.

Each Z is typically —N($R^2$)$_2$, or —O$R^2$. More typically, each Z is —N($R^2$)$_2$. In one embodiment each Z is independently —NHCH$_3$, —N(CH$_3$)$_2$, or —NH$_2$. More preferably each Z is —NH$_2$.

When m is 1, 2 or 3, a moiety -L-Z is typically present at the 5-position of the benzimidazole moiety. In one embodiment, m is 0 or 1. When m is 1 the moiety -L-Z is typically present at the 5-position of the benzimidazole moiety. Preferably, in this embodiment, -L-Z is a CH$_2$NH$_2$ moiety.

In formula (I) n is 1, 2 or 3. For instance it is 1 or 2, or it is 2 or 3.

In formula (I) p is 1, 2 or 3. For instance, it is 1 or 2. Typically p is 1.

In one embodiment of formula (I):
A is an unsubstituted phenyl group or an unsubstituted pyridyl group;
Y is a single bond, —O—, —C(=O)—NH—, or —CH$_2$—;
L is —CH$_2$—;
$R^1$ is a branched, unsubstituted, C$_{4-6}$ alkyl group;
Z is —NH$_2$; and
m is 0 or 1; and
n is 1, 2 or 3.

In a preferred embodiment, the benzimidazole of formula (I) has the following formula (Ia):

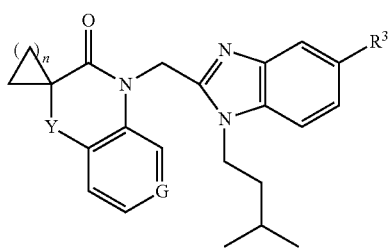

Formula (Ia)

wherein
G is N or CH
Y is a single bond, —O—, —C(=O)—NH—, or —CH$_2$—;
n is 1, 2 or 3; and
$R^3$ is H or —CH$_2$NH$_2$.

Specific examples of compounds of the invention include:
1'-((5-(aminomethyl)-1-isopentyl-1H-benzo[d]imidazol-2yl)methyl)spiro[cyclopentane-1,3'-pyrrolo[2,3-c]pyridin]-2'(1'H)-one;
1'-((5-(aminomethyl)-1-isopentyl-1H-benzo[d]imidazol-2-yl)methyl)spiro[cyclopropane-1,3'-indolin]-2'-one;
1'-((1-isopentyl-1H-benzo[d]imidazol-2-yl)methyl)spiro[cyclopropane-1,3'-indolin]-2'-one;
1'-((5-(aminomethyl)-1-isopentyl-1H-benzo[d]imidazol-2-yl)methyl)spiro[cyclopentane-1,3'-indolin]-2'-one;
1'-((1-isopentyl-1H-benzo[d]imidazol-2-yl)methyl)spiro[cyclopentane-1,3'-indolin]-2'-one;
1'-((5-(aminomethyl)-1-isopentyl-1H-benzo[c/]imidazol-2-yl)methyl)spiro[cyclobutane-1,3'-indolin]-2'-one;
1'-((1-isopentyl-1H-benzo[d]imidazol-2-yl)methyl)spiro[cyclobutane-1,3'-indolin]-2'-one;
4-((5-(aminomethyl)-1-isopentyl-1H-benzo[d]imidazol-2-yl)methyl)spiro[benzo[b][1,4]oxazine-2,1'-cyclopropan]-3 (4H)-one;
4-((1-isopentyl-1H-benzo[d]imidazol-2-yl)methyl)spiro[benzo[b][1,4]oxazine-2,1'-cyclopropan]-3(4H)-one;
1'-((5-(aminomethyl)-1-isopentyl-1H-benzo[d]imidazol-2-yl)methyl)-1'H-spiro[cyclopropane-1,3'-quinolin]-2'(4'H)-one;
1'-((1-isopentyl-1H-benzo[d]imidazol-2-yl)methyl)-1'H-spiro[cyclopropane-1,3'-quinolin]-2'(4'H)-one;
1'-((5-(aminomethyl)-1-isopentyl-1H-benzo[d]imidazol-2-yl)methyl)-1'H-spiro[cyclopentane-1,3'-quinolin]-2' (4'H)-one;
1'-((1-isopentyl-1H-benzo[d]imidazol-2-yl)methyl)-1'H-spiro[cyclopentane-1,3'-quinolin]-2'(4'H)-one; and
1-((1-isopentyl-1H-benzo[d]imidazol-2-yl)methyl)spiro[benzo[e][1,4]diazepine-3,1'-cyclopropane]-2,5(1H,4H)-dione;
and the pharmaceutically acceptable salts thereof.

Preferred compounds of the invention include:
1'-((5-(aminomethyl)-1-isopentyl-1H-benzo[d]imidazol-2yl)methyl)spiro[cyclopentane-1,3'-pyrrolo[2,3-c]pyridin]-2'(1'H)-one;
1'-((5-(aminomethyl)-1-isopentyl-1H-benzo[d]imidazol-2-yl)methyl)spiro[cyclopropane-1,3'-indolin]-2'-one;
1'-((5-(aminomethyl)-1-isopentyl-1H-benzo[d]imidazol-2-yl)methyl)spiro[cyclopentane-1,3'-indolin]-2'-one; and
1'-((5-(aminomethyl)-1-isopentyl-1H-benzo[d]imidazol-2-yl)methyl)spiro[cyclobutane-1,3'-indolin]-2'-one.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of Formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

Compounds of the invention can be prepared according to the following reaction schemes 1 and 2, in which A, Y, L, $R^1$, m and n in the formulae ($I^{Pro}$), (II), and (III) are as defined above for formula (I).

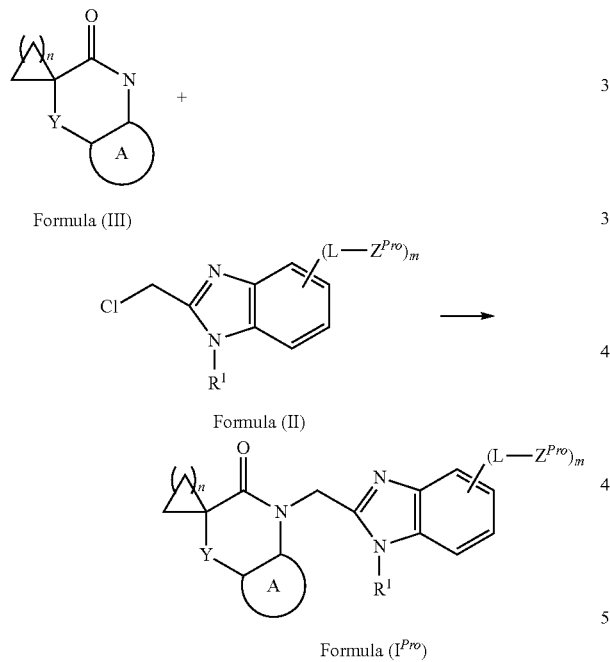

of formula ($I^{Pro}$) in which m is 1, 2, or 3 and $Z^{Pro}$ is Z correspond to a compound of Formula (I) and no deprotection is required.

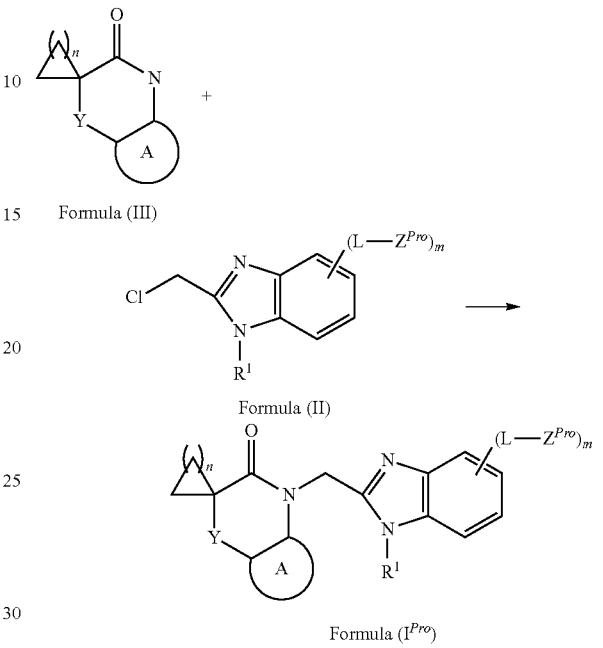

In a further aspect the invention provides a process for producing a compound of the invention as defined above, which comprises treating a compound of formula (III) with a compound of Formula (II):

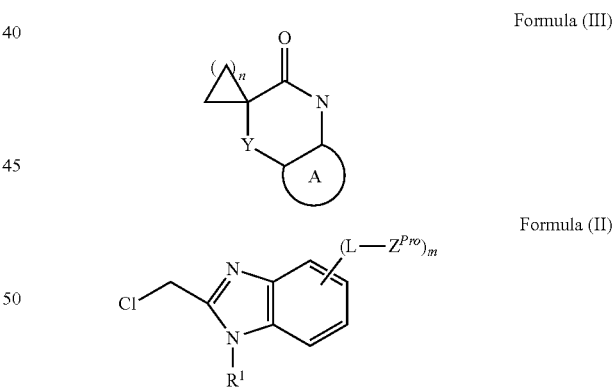

Compounds of Formula (I) in which m is 1, 2, or 3 can be prepared as a compound of Formula ($I^{Pro}$), in which $Z^{Pro}$ is Z, or via a compound of Formula ($I^{Pro}$), in which $Z^{Pro}$ is a protected derivative of Z, as defined above. Suitable protected derivative of Z for any given Z are well known in the art and can be selected by a skilled chemist, e.g. $Z^{Pro}$ may be a BOC-protected amine group when Z is —NH$_2$. The compound of Formula ($I^{Pro}$) can be obtained by reacting a compound of Formula (III) with a compound of Formula (II) under appropriate conditions, e.g. those employed in Examples 1 and 3 below.

Compounds of Formula (I) in which m is zero can be obtained according to the procedure outlined in scheme 1 without any further deprotection step. Likewise, compounds wherein A, Y, L, $R^1$, m and n are as defined above and $Z^{Pro}$ is Z, as defined above, or a protected derivative of Z; and, when m is 1, 2 or 3 and $Z^{Pro}$ is a protected derivative of Z, deprotecting the product obtained.

A benzimidazole of formula (I) can be prepared by deprotecting a compound of formula) ($I^{Pro}$) as defined above in which m is 1, 2, or 3, and $Z^{Pro}$ is a protected derivative of Z, using appropriate reagents and conditions which can readily be determined by one of skill in the art according to the identity of $Z^{Pro}$. For example, when $Z^{Pro}$ is a BOC-protected amine group, the compound of Formula ($I^{Pro}$) can be deprotected with concentrated HCl.

A, Y, L, R$^1$, m and n in the Formulae (I$^{Pro}$), (II), and (III), are as defined above for compounds of Formula (I). Compounds of Formulae (II) and (III) are known compounds, or can be prepared by analogy with known methods.

A benzimidazole of formula (I) can be converted into a pharmaceutically acceptable salt thereof, and a salt can be converted into the free compound, by conventional methods. For instance, a benzimidazole of formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). The compounds are therefore therapeutically useful. Accordingly, the present invention further provides a compound which is a benzimidazole of formula (I), as defined above, or a pharmaceutically acceptable salt thereof, for use in a method of treating the human or animal body by therapy. The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CHF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulisation.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (I) could be administered to a human patient at a dose of between 100-250 mg either once a day, twice or three times a day. For example, a compound of formula (I) could be administered to a human patient at a dose of between 100-250 mg either once a day, twice or three times a day.

The compounds of formula (I) and pharmaceutically acceptable salts thereof may be used on their own. Alternatively, they may be administered in the form of a pharmaceutical composition. The present invention therefore also provides a pharmaceutical composition comprising a compound of formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulfates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin).

The compounds of the invention may, for example, be formulated as aqueous suspensions in a carrier selected from:
(i) 0.5% w/v hydroxypropylmethyl cellulose (HPMC)/0.1% w/v polysorbate 80;
(ii) 0.67% w/v polyvinylpyrrolidone (PVP)/0.33% w/v aerosol AOT (sodium 1,2-bis(2-ethylhexoxycarbonyl)ethanesulphonate);
(iii) 1% w/v pluronic F 127; and
(iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include
(i) RSV nucleocapsid (N)-protein inhibitors;
(ii) other RSV protein inhibitors, such as those that inhibit the phosphoprotein (P) protein and large (L) protein;
(iii) anti-RSV monoclonal antibodies, such as the F-protein antibodies;
(iv) immunomodulating toll-like receptor compounds;
(v) other respiratory virus anti-virals, such as anti-influenza and anti-rhinovirus compounds; and/or
(vi) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (I) or a pharmaceutically acceptable salt thereof as hereinbefore defined in combination with one or more of the therapeutic agents listed as (i) to (vi) above for use in the treatment of RSV.

The following Examples illustrate the invention. They do not however, limit the invention in any way.

EXAMPLES

All temperatures are in ° C. Thin layer chromatography (TLC) was carried out on Si 60G coated Al plates with uv254 indicator (Polygram). All NMR spectra were obtained at 400 MHz in $CDCl_3$ unless stated otherwise.

Analytical LC-MS Conditions

Samples were run on a MicroMass Quattro Ultima, using electrospray with simultaneous positive-negative ion detection.

Column: Phenomenex Luna RP 50×3 mm, 3 μM
Eluents: A—$H_2O$, 0.1% Formic acid; B—MeOH, 0.1% Formic acid

|  | % B | Time/min | Flow ml/min |
|---|---|---|---|
| Gradient: | 5 | 0 | 2.25 |
|  | 37.5 | 2.5 | 2.2 |
|  | 95 | 3.0 | 2.2 |
|  | 95 | 3.5 | 2.3 |
|  | 5 | 3.51 | 2.3 |
|  | 5 | 4.00 | 2.25 |

Detection: HP1100 210-400 nm
Preparative HPLC Conditions
Gradient selected according to analytical HPLC retention time
ie for retention time=3.4 min
Prep column: Phenomenex Luna RP 100×21.2 mm, 5 μM
Solvents: A—HPLC grade Water+0.1% Formic Acid
B—Acetonitrile

| Time (min) | Flowrate (ml/min) | % A | % B | Curve |
|---|---|---|---|---|
| Initial | 20 | 45 | 55 | Initial |
| 0.10 | 20 | 45 | 55 | 6 |
| 7.00 | 20 | 3 | 97 | 6 |
| 10.0 | 20 | 3 | 97 | 6 |
| 10.10 | 20 | 45 | 55 | 6 |
| 12.00 | 20 | 45 | 55 | 6 |

Abbreviations

DCM: Dichloromethane
DIAD Diisopropyl azodicarboxylate
DIPEA: N,N-Di-isopropylethylamine DME: 1,2-Dimethoxyethane
DMF: N,N-Dimethylformamide
DMSO: Dimethyl sulphoxide
EtOAc Ethyl acetate
EtOH EtOH
HATU: O-(7-Azabenzotriazol-1-yl)-N,N,N',N'-tetramethyluronium hexafluorophosphate
HBTU: O-(Benzotriazol-1-yl)-N,N,N',N'-tetramethyluronium hexafluorophosphate
HMDS hexamethyldisilazane
MeCN acetonitrile
MeOH methanol
NMM: N-Methyl morpholine
rt: room temperature
TBTU O-(Benzotriazol-1-yl)-N,N,N',N'-tetramethyluronium tetrafluoroborate
TFA trifluoroacetic acid
THF tetrahydrofuran
TMEDA N,N,N',N'-tetramethylethylenediamine Preparatory Example 1: Ethyl 2-(3-nitropyridin-4-yl)acetate In a dried flask under nitrogen at rt, potassium t-butoxide (22.8 g, 203.4 mmol) in THF (68 mL) was rapidly stirred whilst a solution of 3-nitropyridine (2.1 g, 16.95 mmol) and methyl chloroacetate (2.46 mL, 28.32 mmol) in THF (68 mL) was added dropwise. After 1 hour, 25% aqueous ammonium chloride was added and the mixture extracted with EtOAc. Combined extracts were dried over sodium sulphate, filtered and concentrated in vacuo. Chromatography on silica (20-50% EtOAc in isohexane) gave isolation of the desired compound (1.5 g, 7.63 mmol, 45%).
$^1$H NMR (400 MHz): δ 3.75 (s, 3H), 4.09 (s, 2H), 7.36 (dd, 1H), 8.80 (dd, 1H), 9.32 (d, 1H). LC/MS 197 (MH$^+$).

Preparatory Example 2: Ethyl 1-(3-nitropyridin-4-yl)cyclopentanecarboxylate

Ethyl 2-(3-nitropyridin-4-yl)acetate (265 mg, 1.35 mmol, Preparatory Example 1) in a dried flask under nitrogen was dissolved in MeOH (2.7 mL) was treated with 1,5-diiodobutane (0.9 mL, 6.75 mmol) at rt. Sodium methoxide (6.6 mL of a 0.5 M solution in MeOH) was added dropwise at rt. The resulting deep purple solution was stirred at rt for 16 hours. Water was added to the mixture and then concentrated in vacuo. Partition of the residue between EtOAc and water was followed by extraction of the aqueous phase with EtOAc. Combined organic extracts were dried over sodium sulphate, filtered and concentrated in vacuo. Chromatography on silica (100% isohexane and 25% EtOAc in isohexane) gave isolation of the desired compound (110 mg, 0.44 mmol, 32%).
$^1$H NMR (400 MHz): δ 1.75 (m, 2H), 1.975 (m, 2H), 2.05 (m, 2H), 2.575 (m, 2H), 3.67 (s, 3H), 7.49 (d, 1H), 8.79 (d, 1H), 9.08 (s, 1H). LC/MS 251 (MH$^+$).

Preparatory Example 3: Spiro[cyclopentane-1,3'-pyrrolo[2,3-c]pyridin]-2'(1'H)-one Ethyl 1-(3-nitropyridin-4-yl)cyclopentanecarboxylate (110 mg, 0.44 mmol, Preparatory Example 2) in EtOH (12 mL) was added to a dried flask under nitrogen charged with 10% palladium on carbon (20 mg). The flask was flushed with hydrogen and stirred for 6 hours under this atmosphere of hydrogen. Flushing of the flask with nitrogen was followed by filtration through Celite and concentration in vacuo. The residue was taken up in Et$_2$O (10 mL) and treated with 5 mL of 2 M aqueous hydrochloric acid and stirred for 16 hours. The aqueous phase was separated and concentrated in vacuo.

The residue was treated with titanium trichloride (2 mL of a 40% solution in 20-30% hydrochloric acid) for 6 hours. Solid NaHCO$_3$ was added to neutralize the mixture and the aqueous was extracted with EtOAc. Combined extracts were dried over sodium sulphate filtered and concentrated in vacuo. The desired product was isolated as a white solid (75 mg, 91%).
$^1$H NMR (400 MHz): δ 1.77 (m, 2H), 1.95 (m, 6H), 7.35 (d, 1H), 8.05 (s, 1H), 8.21 (d, 1H), 10.5 (bs, 1H). LC/MS 189 (MH$^+$).

Preparatory Example 4: Spiro[cyclopropane-1,3'-indolin]-2'-one

N-4-methoxybenzyl 3-spirocyclopropyl oxindole (837 mg, 3 mmol) was dissolved in TFA (4.6 mL) under an atmosphere of nitrogen and anisole (0.66 mL, 6 mmol) was added. The mixture was heated at 60° C. for 16 hours. The mixture was cooled to rt and concentrated in vacuo. The residue was taken up in dichloromethane (12 mL). Brine was added and triethylamine (2.5 mL). The aqueous phase was extracted with DCM. Combined extracts were dried over sodium sulphate, filtered and concentrated in vacuo. Chromatography on silica (20-40% EtOAc in isohexane) gave isolation of the desired spirocyclopropyl oxindole as a pale pink solid (318 mg, 2 mmol, 67%).
$^1$H NMR (400 MHz): δ 1.57 (m, 2H), 1.79 (m, 2H), 6.83 (d, 1H), 7.01 (m, 2H), 7.21 (m, 1H), 9.18 (bs, 1H). LC/MS 160 (MH$^+$).

Preparatory Example 5: 1-(4-methoxybenzyl)indolin-2-one

N-(4-methoxybenzyl)isatin (2.67 g) was added portionwise to hydrazine hydrate (20 mL) at rt. The mixture was heated at 95° C. for 40 hours. The mixture was cooled, partitioned between EtOAc and water. The organic phase was washed with brine, dried over sodium sulphate, filtered and concentrated in vacuo to isolate the desired compound as an orange solid (1.82 g, 7.2 mmol, 72%).
$^1$H NMR (400 MHz): δ 3.53 (s, 2H), 3.70 (s, 3H), 4.78 (s, 2H), 6.66 (d, 1H), 6.76 (d, 2H), 6.95 (dd, 1H), 7.10 (dd, 1H), 7.37 (m, 3H). LC/MS 254 (MH$^+$).

Preparatory Example 6: 1'-(4-methoxybenzyl)spiro[cyclopropane-1,3'-indolin]-2'-one In a dried flask under an atmosphere of nitrogen, 1-(4-methoxybenzyl)indolin-2-one (264 mg, 1.04 mmol, Preparatory Example 5) in DMF (1.5 mL) was treated with 1,2-dibromoethane (0.1 mL, 1.18 mmol) and this mixture was cooled to 0° C. Sodium hydride (86 mg, 2.14 mmol) was added portionwise at this temperature. The cooling bath was removed and further sodium hydride (43 mg, 1.07 mmol) was added as the mixture warmed to rt. The mixture was stirred at rt for 16 hours. Ice was added carefully at 0° C. and the resulting suspension was partitioned between EtOAc and water. The organic layer was separated, dried over sodium sulphate, filtered and concentrated in vacuo. Chromatography on silica (isohexane to 50% EtOAc in isohexane) gave isolation of the desired product as a colourless solid (172 mg, 0.61 mmol, 61%).

¹H NMR (400 MHz): δ 1.56 (m, 2H), 1.82 (m, 2H), 3.79 (s, 3H), 4.95 (s, 2H), 6.86 (m, 4H), 7.01 (m, 1H), 7.16 (m, 1H), 7.28 (m, 1H). LC/MS 280 (MH⁺).

Preparatory Example 7: Spiro[cyclopentane-1,3'-indolin]-2'-one n-Butyl lithium (2.5 M in hexanes, 4.2 mL, 0.5 mmol) was added dropwise to a suspension of indolinone (0.665 mg, 5 mmol) and TMEDA (1.5 mL, 10 mmol) in THF (20 mL) at −78° C. in a dried flask under nitrogen. After 1 hour at −78° C., 1,4-diiodobutane (3.3 mL, 25 mmol) was added dropwise and the mixture was allowed to slowly warm to rt. After 12 hours at rt, saturated aqueous ammonium chloride was added to the mixture and this mixture was extracted with EtOAc. The combined organic phases were washed with water, brine, dried over magnesium sulphate, filtered and concentrated in vacuo. Chromatography on silica (10-30% EtOAc in isohexane) gave isolation of the desired compound as a pale pink solid (393 mg, 2.1 mmol, 42%).
¹H NMR (400 MHz): δ 1.90 (m, 2H), 2.03 (m, 2H), 2.10 (m, 2H), 2.21 (m, 2H), 6.94 (m, 1H), 7.04 (m, 1H), 7.20 (m, 2H), 8.75 (bs, 1H). LC/MS 188 (MH⁺).

Preparatory Example 8: N'-phenylcyclobutanecarbohydrazide

In a dried flask under nitrogen, triethylamine (5.4 mL, 48 mmol) was added dropwise to a mixture of phenyl hydrazine hydrochloride (3.92 mL, 40 mmol) in DCM (80 mL) at rt. The mixture was cooled to in an ice/salt bath and cyclobutane carbonyl chloride (4.8 mL, 42 mmol) was added dropwise at a rate to maintain the internal temperature below −10° C. After 1.5 hours at −10° C., the mixture was allowed to warm to rt and stirred there for a further 16 hours. The mixture was concentrated in vacuo and dilute aqueous NaHCO₃ was added. The mixture was filtered and the solid washed with NaHCO₃, Et₂O and dried at the pump to provide the desired compound, as a 2.3-1 mixture with the bis cyclobutane carbohydrazide (5.33 g).
LC/MS 191 (MH⁺)

Preparatory Example 9: Spiro[cyclobutane-1,3'-indolin]-2'-one

To a stirred suspension of calcium oxide (12.6 g, 124 mmol) in quinoline (26 mL) was added N'-phenylcyclobutanecarbohydrazide (4.88 g, 25.6 mmol, Preparatory Example 8). The mixture was heated to 270-310° C. and kept there for 75 minutes. The mixture was cooled to rt and 2 M aqueous hydrochloric acid was added. The mixture was extracted with EtOAc and combined extracts were washed with 2 M hydrochloric acid, brine and dried over Na₂SO₄. Filtration and then concentration in vacuo was followed by chromatography on silica (40-60% EtOAc in hexane) to give isolation of the desired product as an orange solid (1.92 g, 11.1 mmol, 43%).
¹H NMR (400 MHz): δ2.18 (m, 1H), 2.28 (m, 3H), 2.61 (m, 2H), 6.79 (d, 1H), 7.01 (dd, 1H), 7.12 (dd, 1H), 7.41 (d, 1H), 7.95 (bs, 1H). LC/MS 174 (MH⁺).

Preparatory Example 10: 1'-(4-methoxybenzyl)-1'H-spiro[cyclopropane-1,3'-quinolin]-2'(4'H)-one Step 1: 1-(4-methoxybenzyl)-3,4-dihydroquinolin-2(1H)-one (2.678 g, 10 mmol) in THF (10 mL) was added to a freshly prepared solution of LiHMDS (prepared using 4.8 mL of 2.5 M butyllithium in hexanes and 2.1 ml of HMDS) in THF (10 mL) at −78° C. After 1 h at −78° C., this anion solution was added dropwise via cannula to a stirred solution of 1-bromo-2-chloroethane (3 eq, 2.5 mL) in THF (10 mL) at −78° C. The reaction was allowed to warm to rt overnight then quenched by addition of NH₄Cl (aq) and extracted into EtOAc. The organic phase was dried, filtered, concentrated and purified by chromatography on Si with hexane/EtOAc 9:1 to 4:1 as eluent. This gave the chloroethyl compound as an orange oil (1.65 g, approx 70% pure)
Step 2: A solution of the impure 3-(2-chloroethyl)-1-(4-methoxybenzyl)-3,4-dihydroquinolin-2(1H)-one (1.65 g) in acetone (20 mL) was treated with NaI (3.0 g, 4 eq) and heated to reflux for 12 h. The cooled reaction was concentrated and partitioned between water and EtOAc. Sodium thiosulfate was added and the organic phase separated. Concentration gave the iodo compound as an orange oil (2.05 g, approx 70% pure)
Step 3: A solution of 3-(2-iodoethyl)-1-(4-methoxybenzyl)-3,4-dihydroquinolin-2(1H)-one (2.05 g, 4.8 mmol) in THF (10 mL) was added dropwise to a freshly prepared solution of LiHMDS (prepared from BuLi 1 eq, 1.95 mL of 2.5M, and HMDS 1 eq, 1.02 mL) in THF (10 ml) at −78° C. The mixture was stirred for 1 h then was allowed to warm to rt overnight. Brine was added, extracted into EtOAc (2×25 ml), dried, filtered and concentrated to a brown oil (1.05 g, 75%).
¹H NMR (400 MHz): δ 7.26 (s, 1H), 7.11 (m, 5H), 6.90 (m, 5H), 5.30 (d, J=1.0 Hz, 1H), 5.12 (s, 2H), 5.02 (s, 2H), 3.76 (s, 3H), 2.87 (s, 2H), 1.32 (m, 2H), 0.77 (m, 2H). LC/MS 294.5 (MH⁺).
1-(4-methoxybenzyl)-3,4-dihydroquinolin-2(1H)-one was prepared by the method of Winter, D. K. et al, Journal of Organic Chemistry, 75(8), 2610-2618; 2010
¹H NMR (400 MHz): δ 7.07 (m, 4H), 6.83 (m, 4H), 5.04 (s, 2H), 3.70 (s, 3H), 2.89 (dd, J=8.7, 6.0 Hz, 2H), 2.70 (m, 2H)

Preparatory Example 11: 1'H-spiro[cyclopropane-1,3'-quinolin]-2'(4'H)-one

1'-(4-methoxybenzyl)-1'H-spiro[cyclopropane-1,3'-quinolin]-2'(4'H)-one (1.05 g, Preparatory Example 10) was treated with anisole (1 eq) and TFA (3 mL) at 65° C. for 3 h. The cooled mixture was concentrated, taken up in brine/DCM and Et₃N (3 mL) added. The aqueous phase was extracted with DCM (3×10 mL) and the combined organic phases dried and concentrated to a yellow gum (1.5 g). Purification by chromatography on Si with hexane/EtOAc (9:1 to 4:1) as eluent gave the title compound as a white solid (465 mg) which when triturated with isohexane gave, by filtration, the title compound as a white solid (301 mg, 48%).
¹H NMR (400 MHz): δ 8.20 (br s, 1H), 7.21 (m, 1H), 7.11 (m, 1H), 7.01 (td, J=7.5, 1.1 Hz, 1H), 6.78 (dd, J=7.8, 1.2 Hz, 1H), 2.89 (s, 2H), 1.39 (m, 2H), 0.79 (m, 2H). LC/MS 173.95 (M⁺), 205.95.

Preparatory Example 12: 3-(4-Iodobutyl)-1-(4-methoxybenzyl)-3,4-dihydroquinolin-2(1H)-one 1-(4-methoxybenzyl)-3,4-dihydroquinolin-2(1H)-one (1.995 g, 7.4 mmol) in THF (5 mL) was added to a freshly prepared solution of LDA (prepared using 3.58 mL of 2.5 M butyllithium in hexanes and 1.25 mL of diisopropylamine) in THF (5 mL) at −78° C. After 1 h at −78° C., this anion solution was added dropwise via cannula siphon to a stirred solution of 1,4 diiodobutane (2.95 mL, 22.2 mmol, 3 eq) in THF (5 mL) at −78° C. The reaction was allowed to warm to rt overnight then quenched by addition of NH₄Cl (aq) and extracted into EtOAc. The organic phase was dried, filtered, concentrated and purified by chromatography on Si with hexane/EtOAc (9:1 to 4:1) as eluent. This gave the title compound as a pale oil (2.01 g, 60%).

¹H NMR (400 MHz): δ 7.16 (4H, m), 6.98 (1H, t), 6.93 (1H, d), 6.86 (2H, d), 5.12 (2H, s), 3.79 (3H, s), 3.22 (2H, m), 3.08 (1H, dd), 2.78 (1H, dd), 2.68 (1H, m), 1.9 (3H, m), 1.62 (5H, m). LC/MS 450.3.

Preparatory Example 13: 1'-(4-Methoxybenzyl)-1'H-spiro[cyclopentane-1,3'-quinolin]-2'(4'H)-one A solution of 3-(4-iodobutyl)-1-(4-methoxybenzyl)-3,4-dihydroquinolin-2(1H)-one (2 g, 4.4 mmol, Preparatory Example 12) in THF (10 mL) was added dropwise to a solution of LiHMDS (prepared from butyllithium 1.1 eq and HMDS 1.1 eq) in THF (10 mL) at −78° C. The cold bath was removed and the mixture stirred at rt for 2 h. Brine was added and extracted with EtOAc. The combined organic phases were dried and concentrated to an orange oil that was purified by chromatography on Si with Hexane/Et₂O (3:1 to 1:1) as eluent. This gave the title compound as a yellow oil (812 mg, 57%) containing some impurities.

¹H NMR (400 MHz): δ 7.10 (m 3H), 6.94 (t, 1H), 6.84 (m, 3H), 5.09 (s, 2H), 3.76 (s, 3H), 2.85 (s, 2H), 2.13 (m, 2H), 1.75 (m, 5H), 1.52 (m, 2H). LC/MS 322 (MH⁺)

Preparatory Example 14: 1'H-spiro[cyclopentane-1,3'-quinolin]-2'(4'H)-one

A mixture of 1'-(4-methoxybenzyl)-1'H-spiro[cyclopentane-1,3'-quinolin]-2'(4'H)-one (810 mg, 2.5 mmol, Preparatory Example 13) and anisole (1 eq) in TFA (1.9 mL) was heated at 65° C. for 3 h. The mixture was cooled, concentrated in vacuo and taken up in DCM (10 mL). Et₃N (2 mL) was added and the mixture washed with brine. The aqueous phase was extracted with further DCM (2×10 mL) and the combined organic phases dried and concentrated to a light brown solid. Chromatography on Si with Hexane/Et₂O 3:1 to 1:1 give the title compound as a cream solid (373 mg, 74%).

¹H NMR (400 MHz): δ 7.75 (br s, 1H), 7.04 (m, 4H), 3.80 (m, 2H), 2.86 (s, 2H), 2.12 (m, 2H), 1.75 (m, 4H), 1.54 (m, 1H). LC/MS 202 (MH⁺)

Preparatory Example 15: 1-(2-(((1-isopentyl-1H-benzo[d]imidazol-2-yl)methyl)amino)benzamido) cyclopropanecarboxylic Acid DIAD (0.9 mL, 1 eq) in THF (2 mL) was added dropwise to a stirred solution containing (1-isopentyl-1H-benzo[d]imidazol-2-yl)methanol (1.0 g), PPh₃ (1.2 g, 1 eq) and isatoic anhydride (748 mg, 1 eq) in THF (30 mL) and stirred overnight. The reaction was concentrated to a light brown residue that was taken up in DMF (20 mL) and treated with ethyl 1-aminocyclopropanecarboxylate hydrochloride (1.05 g, 1.5 eq) and heated to 75° C. for 48 h. Aqueous workup between Et₂O and water gave a brown foam (|1.2 g). This crude ester was dissolved in 2 M NaOH/EtOH (4:1, 10 mL) and warmed to 70° C. for 5 h. The cooled reaction was concentrated, taken up in 2M NaOH and washed with Et₂O. The aqueous phase was acidified to pH 4 with 2M HCl and extracted into EtOAc (2×25 mL). This gave an impure brown foam which was purified on silica gel with isohexane/EtOAc (3:1 to 1:1) as eluant. This gave the desired acid as the more polar component as a cream solid (279 mg, 15%).

¹H NMR (400 MHz, DMSO): δ 8.85 (1H, s), 8.8 (1H, t), 7.58 (1H, d), 7.48 (1H, d), 7.349 (1H, dd), 7.18 (3H, m), 6.93 (1H, d), 6.55 (1H, t), 4.68 (2H, d), 4.29 (2H, m), 1.67 (1H, sept), 1.578 (2H, m), 1.085 (2H, m), 0.94 (8H, d). LC/MS 421.5 (MH⁺).

Example 1: 1'-((5-(aminomethyl)-1-isopentyl-1H-benzo[d]imidazol-2-yl)methyl)spiro[cyclopentane-1, 3'-pyrrolo[2,3-c]pyridin]-2'(1'H)-one A dried flask under nitrogen was charged with sodium hydride (42 mg, 1.05 mmol) and DMF (0.5 mL). This rapidly stirred suspension was cooled to 0° C. using an ice/water bath and spiro[cyclopentane-1,3'-pyrrolo[2,3-c] pyridin]-2'(1'H)-one (66 mg, 0.35 mmol, Preparatory Example 1) was added dropwise as a solution in DMF (1.2 mL). The ice/water bath was removed for 15 minutes before the mixture was recooled to 0° C. and tert-butyl ((2-(chloromethyl)-1-isopentyl-1H-benzo[d]imidazol-5-yl)methyl) carbamate hydrochloride (143 mg, 0.39 mmol) was added dropwise as a solution in DMF (1.3 mL). The mixture was allowed to warm to rt and stirred for 1.5 hours.

The mixture was cooled to 0° C. and ice was added carefully. Partition between EtOAc and water was followed by separation, drying and concentration in vacuo. The resulting residue was treated with 4 M hydrochloric acid in dioxane (8 mL) at rt for 16 hours. The mixture was partitioned between ethyl acetate and water and the aqueous layer washed with EtOAc. Neutralisation of the aqueous with solid Na₂CO₃ was followed by EtOAc extraction, drying of the combined extracts (Na₂SO₄) and concentration in vacuo. Chromatography on silica (DCM/EtOH/aqueous NH₃, 100/8/1 to 50/8/1) provided isolation of the title compound as a colourless oil. Subsequent freeze drying from MeCN/H₂O (2 mL/1 mL) provided a colourless solid (75 mg, 51%).

¹H NMR (400 MHz): δ 1.01 (d, 6H), 1.58 (m, 2H), 1.71 (m, 1H), 1.90 (m, 2H), 2.02 (m, 2H), 2.15 (m, 2H), 2.16 (m, 2H), 3.99 (s, 2H), 4.26 (m, 2H), 5.26 (s, 2H), 7.13 (d, 2H), 7.27 (m, 2H), 7.70 (d, 1H), 8.37 (d, 1H), 8.77 (s, 1H). LCMS 418 (MH⁺).

Example 2: 1'-((5-(aminomethyl)-1-isopentyl-1H-benzo[d]imidazol-2-yl)methyl)spiro[cyclopropane-1, 3'-indolin]-2'-one In an analogous method to that described in Example 1, spiro[cyclopropane-1,3'-indolin]-2'-one (160 mg, 1 mmol, Preparatory Example 4) was reacted with tert-butyl ((2-(chloromethyl)-1-isopentyl-1H-benzo[d]imidazol-5-yl) methyl)carbamate hydrochloride (366 mg, 1 mmol) to provide 85 mg (0.22 mmol, 22%) of the desired compound as a colourless solid.

¹H NMR (400 MHz): δ 0.90 (d, 6H), 1.46 (m, 2H), 1.59 (m, 2H), 1.69 (m, 2H), 1.82 (m, 2H), 3.99 (s, 2H), 4.24 (m, 2H), 5.34 (s, 2H), 6.83 (d, 1H), 7.01 (d, 1H), 7.26 (m, 2H), 7.45 (d, 1H), 7.73 (s, 1H). LC/MS 389 (MH⁺).

Example 3: 1'-((1-isopentyl-1H-benzo[d]imidazol-2-yl)methyl)spiro[cyclopropane-1,3'-indolin]-2'-one A dried flask under nitrogen was charged with sodium hydride (120 mg, 3.0 mmol) and DMF (1 mL). This rapidly stirred suspension was cooled to 0° C. using an ice/water bath and spiro[cyclopropane-1,3'-indolin]-2'-one (160 mg, 1.0 mmol, Preparatory Example 4) was added dropwise as a solution in DMF (2 mL). The ice/water bath was removed for 15 minutes before the mixture was recooled to 0° C. and 2-(chloromethyl)-1-isopentyl-1H-benzo[d]imidazole hydrochloride (236 mg, 1.0 mmol) was added dropwise as a solution in DMF (2.1 mL). The mixture was allowed to warm to rt and stirred there for 16 hours.

The mixture was cooled to 0° C. and ice was added carefully. Partition between EtOAc and water was followed by separation, drying and concentration in vacuo. Preparative HPLC gave isolation of the desired compound, (110 mg, 0.31 mmol, 31%).

$^1$H NMR (400 MHz): δ 0.96 (d, 6H), 1.45 (m, 2H), 1.60 (m, 2H), 1.69 (m, 1H), 1.82 (m, 2H), 4.26 (m, 2H), 5.35 (s, 2H), 6.83 (d, 1H), 7.02 (dd, 1H), 7.19 (dd, 1H), 7.29 (m, 3H), 7.47 (d, 1H), 7.81 (m, 1H). LC/MS 360 (MH$^+$).

Example 4: 1'-((5-(aminomethyl)-1-isopentyl-1H-benzo[d]imidazol-2-yl)methyl)spiro[cyclopentane-1,3'-indolin]-2'-one In an analogous method to that described in Example 1, spiro[cyclopentane-1,3'-indolin]-2'-one (187 mg, 1 mmol) was reacted with tert-butyl ((2-(chloromethyl)-1-isopentyl-1H-benzo[d]imidazol-5-yl)methyl)carbamate hydrochloride (366 mg, 1 mmol) to provide 65 mg (0.22 mmol, 22%) of the desired compound as a colourless solid.

$^1$H NMR (400 MHz): δ 1.00 (d, 6H), 1.55 (m, 2H), 1.70 (bs, 2H), 1.74 (m, 1H), 1.88 (m, 2H), 2.03 (m, 2H), 2.13 (m, 2H), 2.22 (m, 2H), 3.99 (s, 2H), 4.25 (m, 2H), 5.25 (s, 2H), 7.03 (m, 1H), 7.19 (m, 2H), 7.28 (m, 2H), 7.46 (d, 1H), 7.72 (s, 1H). LC/MS 417 (MH$^+$).

Example 5: 1'-((1-isopentyl-1H-benzo[d]imidazol-2-yl)methyl)spiro[cyclopentane-1,3'-indolin]-2'-one In an analogous method to that described in Example 3, spiro[cyclopentane-1,3'-indolin]-2'-one (187 mg, 1 mmol, Preparatory Example 7) was reacted with 2-(chloromethyl)-1-isopentyl-1H-benzo[d]imidazole hydrochloride (238 mg, 1 mmol) to provide 60 mg (0.22 mmol, 15%) of the desired compound as a colourless solid.

$^1$H NMR (400 MHz): δ 0.91 (d, 6H), 1.58 (m, 2H), 1.65 (m, 1H), 1.9-2.15 (m, 6H), 4.18 (m, 2H), 5.15 (s, 2H), 6.93 (m, 1H), 7.10 (m, 2H), 7.19 (m, 2H), 7.21 (m, 1H), 7.38 (m, 1H), 7.71 (m, 1H). LC/MS 388 (MH$^+$).

Example 6: 1'-((5-(aminomethyl)-1-isopentyl-1H-benzo[d]imidazol-2-yl)methyl)spiro[cyclobutane-1,3'-indolin]-2'-one In an analogous method to that described in Example 1, spiro[cyclobutane-1,3'-indolin]-2'-one (173 mg, 1 mmol, Preparatory Example 9) was reacted with tert-butyl ((2-(chloromethyl)-1-isopentyl-1H-benzo[d]imidazol-5-yl)methyl)carbamate hydrochloride (366 mg, 1 mmol) to provide 72 mg (0.22 mmol, 18%) of the desired compound as a colourless solid.

$^1$H NMR (400 MHz): δ 0.98 (d, 6H), 1.49 (m, 2H), 1.72 (m, 1H), 1.75 (bs, 2H), 2.35 (m, 4H), 2.74 (m, 2H), 3.99 (s, 2H), 4.25 (m, 2H), 5.22 (s, 2H), 7.08 (m, 1H), 7.20 (m, 1H), 7.26 (m, 2H), 7.40 (d, 1H), 7.51 (dd, 1H), 7.71 (s, 1H). LC/MS 403 (MH$^+$).

Example 7: 1'-((1-isopentyl-1H-benzo[d]imidazol-2-yl)methyl)spiro[cyclobutane-1,3'-indolin]-2'-one In an analogous method to that described in Example 3, spiro[cyclobutane-1,3'-indolin]-2'-one (126 mg, 0.58 mmol, Preparatory Example 9) was reacted with 2-(chloromethyl)-1-isopentyl-1H-benzo[d]imidazole hydrochloride (122 mg, 1 mmol) to provide 69 mg (0.18 mmol, 32%) of the desired compound as a colourless solid.

$^1$H NMR (400 MHz): δ 0.99 (d, 6H), 1.52 (m, 2H), 1.72 (m, 1H), 2.39 (m, 4H), 2.74 (m, 2H), 4.28 (m, 2H), 5.24 (s, 2H), 7.09 (dd, 1H), 7.21 (dd, 2H), 7.28 (m, 3H), 7.51 (d, 1H), 7.52 (d, 1H), 7.80 (m, 1H). LC/MS 374 (MH$^+$).

Example 8: 4-((5-(aminomethyl)-1-isopentyl-1H-benzo[d]imidazol-2-yl)methyl)spiro[benzo[b][1,4]oxazine-2,1'-cyclopropan]-3(4H)-one By an analogous method to Example 1, spiro[benzo[b][1,4]oxazine-2,1'-cyclopropan]-3(4H)-one (125 mg, 0.71 mmol) was reacted with tert-butyl ((2-(chloromethyl)-1-isopentyl-1H-benzo[d]imidazol-5-yl)methyl)carbamate hydrochloride (0.7 mmol) to provide the title compound as a cream solid (149 mg, 49%).

$^1$H NMR (400 MHz): δ 7.65 (m, 2H), 7.27 (m, 2H), 6.99 (dt, J=7.6, 1.5 Hz, 2H), 6.86 (dd, J=7.8, 1.6 Hz, 1H), 5.55 (s, 2H), 4.19 (m, 2H), 3.98 (s, 2H), 1.75 (dp, J=13.2, 6.6 Hz, 1H), 1.59 (m, 6H), 1.47 (m, 2H), 1.29 (m, 2H), 1.02 (d, J=6.6 Hz, 6H),). LC/MS 405 (MH$^+$).

Spiro[benzo[b][1,4]oxazine-2,1'-cyclopropan]-3(4H)-one was prepared by the method of Powell et al, J. Med. Chem 15 (2007) 5912

$^1$H NMR (400 MHz): δ 8.53 (s, 1H), 6.91 (m, 4H), 1.46 (m, 2H), 1.26 (m, 2H)

Example 9: 4-((1-isopentyl-1H-benzo[d]imidazol-2-yl)methyl)spiro[benzo[b][1,4]oxazine-2,1'-cyclopropan]-3(4H)-one By an analogous method to Example 3, spiro[benzo[b][1,4]oxazine-2,1'-cyclopropan]-3(4H)-one (125 mg, 0.71 mmol) was reacted with 2-(chloromethyl)-1-isopentyl-1H-benzo[d]imidazole hydrochloride (0.7 mmol) to give, after purification by RP HPLC, the title compound as a white solid (46 mg, 17%).

$^1$H NMR (400 MHz): δ 7.74 (m, 1H), 7.64 (dd, J=8.0, 1.6 Hz, 1H), 7.26 (m, 3H), 6.98 (dtd, J=27.6, 7.6, 1.6 Hz, 2H), 6.84 (dd, J=7.9, 1.6 Hz, 1H), 5.54 (s, 2H), 4.19 (m, 2H), 1.73 (m, 2H), 1.58 (m, 1H), 1.47 (q, J=5.2 Hz, 2H), 1.27 (q, J=5.1 Hz, 2H), 1.00 (d, J=6.6 Hz, 6H).). LC/MS 376 (MH$^+$).

Spiro[benzo[b][1,4]oxazine-2,1'-cyclopropan]-3(4H)-one was prepared by the method of Powell et al, J. Med. Chem 15 (2007) 5912

$^1$H NMR (400 MHz): δ 8.53 (s, 1H), 6.91 (m, 4H), 1.46 (m, 2H), 1.26 (m, 2H)

Example 10: 1'-((5-(aminomethyl)-1-isopentyl-1H-benzo[d]imidazol-2-yl)methyl)-1'H-spiro[cyclopropane-1,3'-quinolin]-2'(4'H)-one By an analogous method to Example 1, 1'H-spiro[cyclopropane-1,3'-quinolin]-2'(4'H)-one (150 mg, 0.85 mmol, Preparatory Example 11) was reacted with text-butyl ((2-(chloromethyl)-1-isopentyl-1H-benzo[d]imidazol-5-yl)methyl)carbamate hydrochloride (348 mg) to provide the title compound as a cream foam (93 mg, 27%)

$^1$H NMR (400 MHz): δ7.65 (m, 2H), 7.25 (m, 3H), 7.04 (m, 2H), 5.54 (s, 2H), 4.21 (m, 2H), 3.96 (s, 2H), 2.86 (s, 2H), 1.85 (br m, 4H), 1.70 (m, 2H), 1.41 (q, J=4.0 Hz, 2H), 1.02 (d, J=6.5 Hz, 6H), 0.82 (m, 3H). LC/MS 403 (MH$^+$).

Example 11: 1'-((1-isopentyl-1H-benzo[d]imidazol-2-yl)methyl)-1'H-spiro[cyclopropane-1,3'-quinolin]-2'(4'H)-one By an analogous method to Example 3, 1'H-spiro[cyclopropane-1,3'-quinolin]-2'(4'H)-one (154 mg, 0.8 mmol, Preparatory Example 11) was reacted with 2-(chloromethyl)-1-isopentyl-1H-benzo[d]imidazole hydrochloride (0.8 mmol) to give, after purification by RP HPLC, the title compound as a white solid (52 mg, 17%)

$^1$H NMR (400 MHz): δ7.74 (1H, m), 7.67 (1H, d), 7.278 (4H, m), 7.074 (1H, d), 7.017 (1H, t), 5.56 (2H, s), 4.23 (2H, m), 2.86 (2H, s), 1.77 (1H, sept), 1.65 (14H, m), 1.41 (2H, m), 1.03 (6H, d), 0.82 (2H, m). LC/MS 374 (MH$^+$).

Example 12: 1'-((5-(aminomethyl)-1-isopentyl-1H-benzo[d]imidazol-2-yl)methyl)-1'H-spiro[cyclopentane-1,3'-quinolin]-2'(4'H)-one By an analogous method to Example 1, 1'H-spiro[cyclopentane-1,3'-quinolin]-2'(4'H)-one (125 mg, 0.62 mmol, Preparatory Example 14) was reacted with tert-butyl ((2-(chloromethyl)-1-isopentyl-1H-benzo[d]imidazol-5-yl)methyl)carbamate hydrochloride (1 eq) to give the title compound as a pale foam (101 mg, 38%).

$^1$H NMR (400 MHz): δ 7.65 (s, 1H), 7.58 (d, 1H), 7.25 (m, 4H), 7.12 (dd, J=7.4, 1.5 Hz, 1H), 6.98 (td, J=7.4, 1.0 Hz, 1H), 5.52 (s, 2H), 4.24 (m, 2H), 3.96 (s, 2H), 2.86 (s, 2H), 2.16 (m, 2H), 1.76 (m, 5H), 1.63 (m, 8H), 1.53 (m, 2H), 1.02 (d, J=6.5 Hz, 6H). LC/MS 431.5 (MH$^+$).

Example 13: 1'-((1-isopentyl-1H-benzo[d]imidazol-2-yl)methyl)-1'H-spiro[cyclopentane-1,3'-quinolin]-2'(4'H)-one By an analogous method to Example 3, 1'H-spiro[cyclopentane-1,3'-quinolin]-2'(4'H)-one (125 mg, 0.62 mmol) was reacted with 2-(chloromethyl)-1-isopentyl-1H-benzo[d]imidazole hydrochloride (0.62 mmol) and purified by RP-HPLC to give the title compound as a pale foam (80 mg, 32 mg).

$^1$H NMR (400 MHz): δ7.64 (m, 1H), 7.51 (d, J=8.2 Hz, 1H), 7.16 (m, 4H), 7.02 (dd, J=7.3, 1.6 Hz, 1H), 6.89 (td, J=7.4, 1.1 Hz, 1H), 5.44 (s, 2H), 4.15 (m, 2H), 2.76 (s, 2H), 2.06 (m, 2H), 1.58 (m, 9H), 0.93 (d, J=6.5 Hz, 6H). LC/MS 402.4 (MH$^+$).

Example 14: 1-((1-isopentyl-1H-benzo[d]imidazol-2-yl)methyl)spiro[benzo[e][1,4]diazepine-3,1'-cyclopropane]-2,5(1H,4H)-dione A solution of 1-(2-(((1-isopentyl-1H-benzo[d]imidazol-2-yl)methyl)amino)benzamido)cyclopropanecarboxylic acid (279 mg, Preparatory Example 15) in DMF (5 mL) was treated with TBTU (284 mg, 1.2 eq) and DIPEA (190 μL, 1.3 eq) then stirred for 12 h at rt. After concentrating in vacuo, the residue was partitioned between Et$_2$O and 2M NaOH. The Et$_2$O phase was separated, dried and concentrated before being purified by chromatography on Si gel with isohexane/EtOAC (4:1) as eluant. This gave the title compound as a gum, which was freeze-dried from an aq MeCN solution to give a grey powder (42 mg, 16%) $^1$H NMR (400 MHz) δ 8.3 (1H, t), 7.2 (1H, dd), 7.68 (1H, m), 7.24 (4H, m), 6.91 (1H, dm), 6.67 (1H, ddd), 4.68 (2H, d), 4.11 (2H, m), 1.75 (2H, m), 1.72 (2H, m), 1.58 (2H, m), 0.88 (6H, d). LC/MS 403.2 (MH$^+$).

Example 15: Biological Testing

Compounds of the Invention, Prepared as Described in the Preceding Examples, were Submitted to the Following Biological Assay:

Plaque Reduction Assay

The compounds of Examples 1-13 were presented for assay as a pre-weighed quantity equivalent to 100$^{th}$ of their molecular weight. Addition of 1.00 mL of 100% cell culture grade dimethylsulfoxide (DMSO) provided a stock solution of 10 mM concentration. Dissolution if required was aided by sonication at room temperature or by gentle warming (<40° C.) with aspiration by pipette.

Subsequently, aliquots were removed from the DMSO stock and diluted to the required concentration by the addition of a buffer appropriate to the assay to a final concentration containing not less than 0.5% DMSO. The 100% DMSO stock solution was stored at 4° C. as required with protection from light and adventitious moisture. It was allowed to thaw gently overnight and if solid was obvious, aspirated or otherwise re-solubilised before removal of an aliquot.

Plaque Reduction Assay:

Vero cells were seeded in 96-well plates in a volume of 100 μL of Optimem supplemented with 3% FCS at a concentration of 4×10$^4$ cells per well. After an overnight incubation at 37° C. in a humidified 5% CO$_2$ atmosphere, the monolayer of cells should be approximately 90% confluent. Antiviral compounds were titrated in pre-warmed Serum Free (SF) Optimem in a U-bottom 96 well plate. For compounds in a DMSO solution, titration in 100% DMSO was performed first and each concentration added individually to a 2× final concentration at 4% DMSO in SF media before mixing with virus (2% final DMSO with virus). Media was then removed from cells and replaced with PBS (100 μl/well). RSV stock was thawed and diluted in SF Optimem media to 4000 PFU/mL1. An equal volume of virus was added to compounds on the titration plate. PBS was removed from cells which were then inoculated with the virus/compound solution (50 μL/well). Cells were incubated for 2 h in a 37° C.+5% CO$_2$ humidified incubator to allow infection. Inoculum was removed and media (Optimem+1% FCS) added to cells (100 μl/well). Cells were subsequently incubated for 48 h at 37° C.+5% CO$_2$ in a humidified incubator.

Immunostaining Procedure:

Media was removed from cells and the monolayer washed with PBS. Cells were fixed with ice cold 80% Acetone in PBS (100 μl/well) for 20 mins at −20° C. Fixative was removed and cells are dried for 30 mins with plates inverted. Blocking solution (5% skim milk powder in PBS-T) was added to cells (150 μL/well) and plates were incubated for 30 mins at room temperature. Blocking solution was removed and plates washed once with PBS-T. Primary antibody in blocking solution was added to plates (50 μl/well) and incubated for 1 h at 37° C. Plates were then washed 3 times with PBS-T. Secondary antibody in blocking solution was added to plates (50 μL/well) and incubated for 1 h at 37° C. in the dark. Plates were washed as above and then dried for 10 mins. Plates were scanned on the Odyssey Imager (Li-Cor Biosciences) at a resolution of 42 μM, medium quality and level 5 intensity in the 800 nM channel.

Data Analysis:

Images obtained were saved and plaque numbers counted with the aid of computer imaging software. EC$_{50}$ values for compounds were derived from dose response curves [three variable log(inhibitor) vs response] obtained using Graphpad Prism software.

Results:

All compounds tested were found to have an $EC_{50}$ of 80 µM or lower.

Example 16: Aqueous Formulation

The compound of Example 10 is formulated as a solution in 30% w/v captisol (i.e. sulfobutylether-beta-cyclodextrin) at pH4 according to the following procedure.

A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 10 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 17: Tablet Composition

Tablets, each weighing 0.15 g and containing 25 mg of a compound of the invention are manufactured as follows:

Composition for 10,000 Tablets

Compound of the invention (250 g)

Lactose (800 g)

Corn starch (415 g)

Talc powder (30 g)

Magnesium stearate (5 g)

The compound of the invention, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 18: Injectable Formulation

| Compound of the invention | 200 mg |
| Hydrochloric Acid Solution 0.1M or Sodium Hydroxide Solution 0.1M q.s. to pH | 4.0 to 7.0 |
| Sterile water q.s. to | 10 mL |

The compound of the invention is dissolved in most of the water (35° C.-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 19 Intramuscular Injection

| Compound of the invention | 200 mg |
| Benzyl Alcohol | 0.10 g |
| Glycofurol 75 | 1.45 g |
| Water for injection q.s to | 3.00 ml |

The compound of the invention is dissolved in the glycofurol. The benzyl alcohol is then added and dissolved, and water added to 3 mL. The mixture is then filtered through a sterile micropore filter and sealed in sterile 3 mL glass vials (type 1).

Example 20 Syrup Formulation

| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbital solution and finally the flavour. The volume is made up with purified water and mixed well.

The invention claimed is:

1. A compound which is a benzimidazole of formula (I):

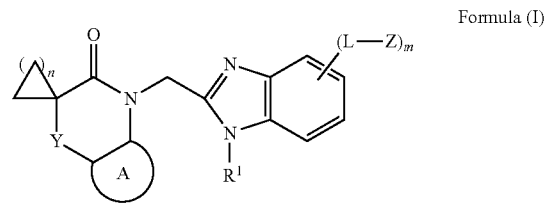

Formula (I)

wherein:
A is phenyl or 6-membered heteroaryl, each of which is unsubstituted or substituted by 1, 2 or 3 groups Q;
Y is a single bond, —O—, —C(═O)—N(R$^2$)—, or —(CH$_2$)$_p$—;
each L is independently $C_{1-3}$ alkylene;
R$^1$ is linear or branched $C_{1-6}$ alkyl, which is unsubstituted or substituted by 1, 2 or 3 groups Q;
each Z is independently —N(R$^2$)$_2$ or —OR$^2$;
each R$^2$ is independently hydrogen or $C_{1-4}$ alkyl;
m is 0 or 1;
n is 1, 2, or 3;
p is 1 or 2; and
Q is halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —CO$_2$R′″, —NR′″$_2$, —SR′″, —S(═O)R′″ or —S(═O)$_2$R′″, wherein each R′″ is independently selected from H and $C_{1-6}$ alkyl;
or a pharmaceutically acceptable salt thereof.

2. A compound according to claim 1, wherein R$^1$ is a linear or branched $C_{3-6}$ alkyl.

3. A compound according to claim 1 wherein, in formula (I):

A is phenyl group or a pyridyl group which is unsubstituted or substituted by 1, 2, or 3 halo groups;
Y is a single bond, —O—, —C(=O)—NH—, or —CH$_2$—;
L is —CH$_2$—;
R$^1$ is a linear or branched C$_{4-6}$ alkyl group which is unsubstituted or substituted by 1, 2, or 3 halo groups;
Z is —NH$_2$;
m is 0 or 1; and
n is 1, 2 or 3.

4. A compound according to claim 1 wherein the benzimidazole of formula (I) has the following formula (a):

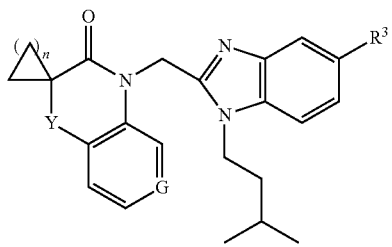

Formula (Ia)

wherein
G is N or CH
Y is a single bond, —O—, —C(=O)—NH—, or —CH$_2$—;
n is 1, 2 or 3; and
R$^3$ is H or —CH$_2$NH$_2$.

5. A compound according to claim 3 wherein, in formula (I), A is an unsubstituted phenyl group or an unsubstituted pyridyl group.

6. A compound according to claim 1 which is selected from
1'-((5-(aminomethyl)-1-isopentyl-1H-benzo[d]imidazol-2-yl)methyl)spiro[cyclopentane-1,3'-pyrrolo[2,3-c]pyridin]-2'(1'H)-one;
1'-((5-(aminomethyl)-1-isopentyl-1H-benzo[d]imidazol-2-yl)methyl)spiro[cyclopropane-1,3'-indolin]-2'-one;
1'-((1-isopentyl-IH-benzo[d]imidazol-2-yl)methyl)spiro[cyclopropane-1,3'-indolin]-2'-one;
1'-((5-(aminomethyl)-1-isopentyl-1H-benzo[d]imidazol-2-yl)methyl)spiro[cyclopentane-1,3'-indolin]-2'-one;
1'-((1-isopentyl-IH-benzo[d]imidazol-2-yl)methyl)spiro[cyclopentane-1,3'-indolin]-2'-one;
1'-((5-(aminomethyl)-1-isopentyl-1H-benzo[d]imidazol-2-yl)methyl)spiro[cyclobutane-1,3'-indolin]-2'-one;
1'-((1-isopentyl-1H-benzo[d]imidazol-2-yl)methyl)spiro[cyclobutane-1,3'-indolin]-2'-one;
4-((5-(aminomethyl)-1-isopentyl-1H-benzo[d]imidazol-2-yl)methyl)spiro[benzo[b][1,4]oxazine-2,1'-cyclopropan]-3(4H)-one;
4-((1-isopentyl-1H-benzo[d]imidazol-2-yl)methyl)spiro[benzo[b][1,4]oxazine-2,1'-cyclopropan]-3(4H)-one;
1'-((5-(aminomethyl)-1-isopentyl-1H-benzo[d]imidazol-2-yl)methyl)-1'H-spiro[cyclopropane-1,3'-quinolin]-2'(4'H)-one;
1'-((1-isopentyl-1H-benzo[d]imidazol-2-yl)methyl)-1'H-spiro[cyclopropane-1,3'-quinolin]-2'(4'H)-one;
1'-((5-(aminomethyl)-1-isopentyl-1H-benzo[d]imidazol-2-yl)methyl)-1'H-spiro[cyclopentane-1,3'-quinolin]-2'(4'H)-one;
1'-((1-isopentyl-1H-benzo[d]imidazol-2-yl)methyl)-1'H-spiro[cyclopentane-1,3'-quinolin]-2'(4'H)-one; and
1-((1-isopentyl-1H-benzo[d]imidazol-2-yl)methyl)spiro[benzo[e][1,4]diazepine-3,1'-cyclopropane]-2,5(1H,4H)-dione;
and the pharmaceutically acceptable salts thereof.

7. A pharmaceutical composition which comprises a compound as defined in claim 1, and a pharmaceutically acceptable carrier or diluent.

8. A product containing:
(a) a compound as defined in claim 1; and
(b) one or more further therapeutic agents.

9. A product according to claim 8, wherein the further therapeutic agent is:
(i) a RSV nucleocapsid (N)-protein inhibitor;
(ii) another protein inhibitor;
(iii) an anti-RSV monoclonal antibody;
(iv) an immunomodulating toll-like receptor compound;
(v) another respiratory virus anti-viral; and/or
(vi) an anti-inflammatory compound.

10. A pharmaceutical composition which comprises (a) a compound as defined in claim 1, and (b) one or more further therapeutic agents, together with a pharmaceutically acceptable carrier or diluent.

* * * * *